United States Patent [19]

Pommier et al.

[11] Patent Number: 5,622,960
[45] Date of Patent: Apr. 22, 1997

[54] TOPOISOMERASE II INHIBITORS AND THERAPEUTIC USES THEREFOR

[75] Inventors: Yves Pommier, Bethesda, Md.; Timothy L. MacDonald; Jose S. Madalengoitia, both of Charlottesville, Va.

[73] Assignee: The United States of America as represented by the Department of Health and Human Services, Washington, D.C.

[21] Appl. No.: 965,922

[22] Filed: Oct. 23, 1992

Related U.S. Application Data

[63] Continuation-in-part of Ser. No. 868,408, Apr. 14, 1992, abandoned.

[51] Int. Cl.$^6$ .......................... C07D 471/00; A61K 31/44
[52] U.S. Cl. ................................................ 514/287; 546/64
[58] Field of Search .............................. 546/64; 514/287

[56] References Cited

U.S. PATENT DOCUMENTS

| | | | |
|---|---|---|---|
| 3,476,764 | 11/1969 | Wagner | 546/64 |
| 3,655,671 | 4/1972 | Suh et al. | 546/64 |
| 3,880,870 | 4/1975 | Ledig et al. | 546/64 |
| 3,917,599 | 11/1975 | Saxena et al. | 546/64 |
| 5,053,431 | 10/1991 | Watanabe et al. | 514/649 |
| 5,064,823 | 11/1991 | Lee et al. | 514/198 |
| 5,126,351 | 6/1992 | Luzzio et al. | 514/291 |
| 5,132,322 | 7/1992 | Lee et al. | 514/468 |

FOREIGN PATENT DOCUMENTS 0357122  3/1990  European Pat. Off. .

OTHER PUBLICATIONS

B. H. Long, "Structure–Activity Relationships of Podophyllin Congeners That Inhibit Topoisomerase II", DNA Topoisomerases in Cancer Therapy, NCI Monographs, No. 4, 1987, pp. 123–127.

Zwelling, et al., "Topoisomerase II as a Target of Antileukemic Drugs", DNA Topoisomerases in Cancer Therapy, NCI Monographs, No. 4, 1987, pp. 79–82.

Kohn, et al., "Topoisomerase II as a Target of Anticancer Drug Action in Mammalian Cells", DNA Topoisomerases in Cancer Therapy, NCI Monographs, No. 4, 1987, pp. 61–71.

J. C. Wang, "DNA Topoismerases: From a Laboratory Curiosity to a Subject in Cancer Chemotherapy", DNA Topoisomerases in Cancer Therapy, NCI Monographs, No. 4, 1987, pp. 3–6.

Chen, et al., "DNA Topoisomerases as Therapeutic Targets in Cancer Chemotherapy", Chapter 4, Annual Reports in Medical Chemistry, vol. 21, 1986, pp. 257–262.

Nelson, et al., "Mechanism of Antitumor Drug Action: Poisoning of Mammalian DNA Topoiosomerase II on DNA by 4'–(9–acridinylamino)–methanesulfon–m–anisidide", Proc. Natl. Acad. Sci. vol. 81, 1984, pp. 1361–1365.

Yang, et al., "Identification of DNA Topoisomerase II as an Intracellular Target of Antitumor Epipodophyllotoxins in Simian Virus 40–Infected Monkey Cells", Cancer Research, vol. 45, 1985, pp. 5872–5876.

L. F. Liu, "DNA Topoisomerase Poins as Antitumor Drugs", Annu. Rev. Biochem., vol. 58, 1989, pp. 351–375.

Macdonald, et al., "On the Mechanism of Interaction of DNA Topoisomerase II with Chemotherapeutic Agents", DNA Topoisomerases in Cancer, Chapter 16, 1991, pp. 199–214.

M. R. Boyd, "Status of the NCI Preclinical Antitumor Drug Discovery Screen", Principles & Practice of Oncology, vol. 3, No. 10, 1989, pp. 1–12.

Monks, et al., "Feasibility of a High–Flux Anticancer Drug Screen Using a Diverse Panel of Cultured Human Tumor Cell Lines", Journal of the National Cancer Inst., Articles, vol. 83, No. 11, 1991, pp. 757–766.

Paull, et al., "Display and Analysis of Patterns of Differential Activity of Drugs Against Human Tumor Cell Lines: Development of Mean Graph and Compare Algorithm", Journal of the National Cancer Institute, Reports, vol. 18, No. 14, 1989, pp. 1089–1092.

Cancer Research, vol. 52, No. 16, Aug. 15, 1992, pp. 4478–4483, F. Leteurtre et al. "Rational design and molecular effects of a new topoisomerase II inhibitor, azatoxin".

Primary Examiner—Richard D. Lovering
Assistant Examiner—Catherine Scalzo
Attorney, Agent, or Firm—Foley & Lardner

[57] ABSTRACT

Azatoxin and derivatives thereof are illustrative of a new class of antitumor drugs that are topoisomerase II (top 2) inhibitors. The pharmacophore inhibits the catalytic activity of the purified enzyme but does not unwind relaxed or supercoiled DNA. It is nonintercalative and has at least two domains: a quasi-planar polycyclic ring system, which may bind between DNA base pairs, and a pendant substituent thought to interact with the enzyme, with the DNA grooves or with both. In SV40 and c-myc DNA, azatoxin induces numerous double-strand breaks according to a cleavage pattern which differs from those of known top 2 inhibitors. Azatoxin also is a potent inhibitor of tubulin polymerization.

9 Claims, 5 Drawing Sheets

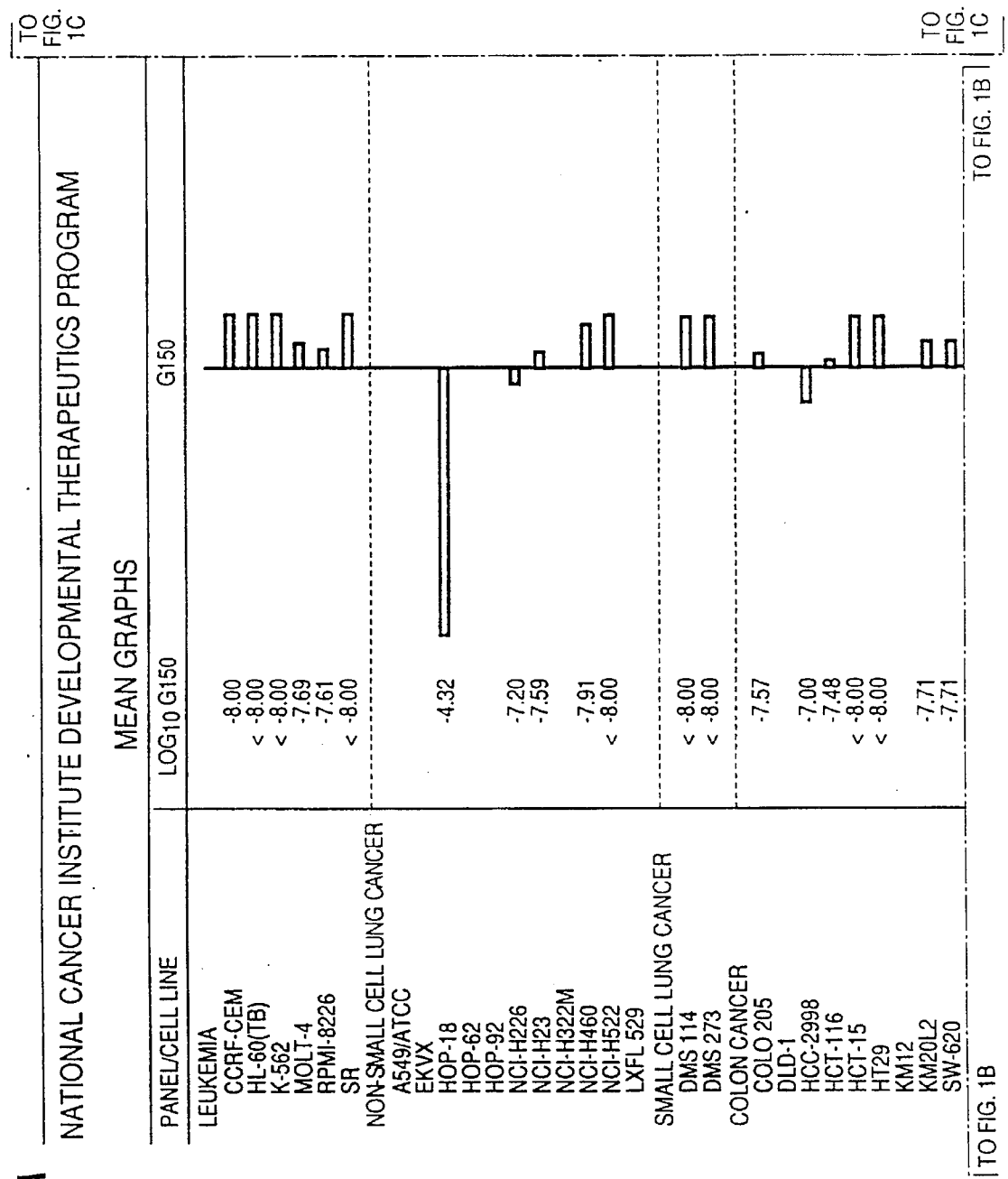

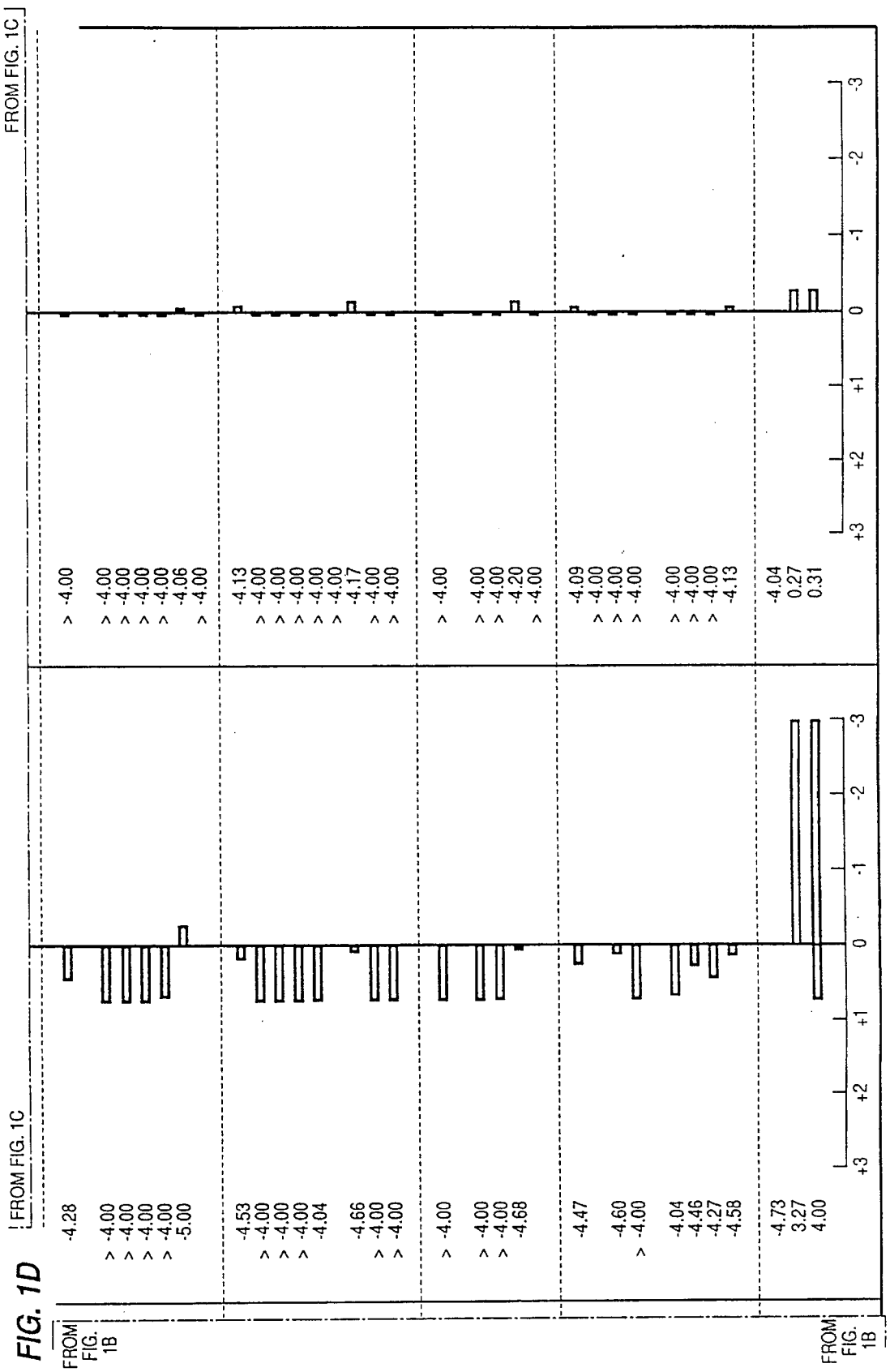

TOPOISOMERASE II INHIBITORS AND THERAPEUTIC USES THEREFOR

This application is a continuation-in-part of application Ser. No. 07/868,408, filed Apr. 14, 1992, now abandoned the disclosure of which is herein incorporated by reference.

BACKGROUND OF THE INVENTION

Enzymes categorized under the rubric of "DNA topoisomerase" control the topology of DNA over the course of conformational and topological changes which occur during many cellular processes. For example, DNA topoisomerases are involved in DNA replication, RNA transcription and recombination.

Two kinds of DNA topoisomerases are recognized generally. Type I and type II enzymes catalyze topological changes in DNA by transiently breaking one strand or two strands of the DNA helix, respectively. The relaxation of superhelical DNA is a characteristic reaction catalyzed by a topoisomerase I ("top 1"), while a topoisomerase II ("top 2") catalyzes the passing of two DNA segments in a manner leading to such topoisomerization reactions of DNA as supercoiling/relaxation, knotting/unknotting and catenation/decantenation.

DNA topoisomerase II has been implicated as the chemotherapeutic target for a diverse group of antitumor agents, including epipodophyllotoxins, anthracyclines, acridines, anthracenediones and ellipticines. See Macdonald et al., in DNA TOPOISOMERASES IN CANCER 199–214 (Oxford University Press 1991) (hereafter "Macdonald (1991)"), the contents of which are hereby incorporated by reference. Under the influence of such drugs, top 2 is believed to cleave DNA and form a concomitant covalent association with the broken strand(s) of duplex DNA. The formation of such "cleavable complexes" of drug, DNA and top 2 enzyme has been attributed to the stabilization by the drug of a covalent, DNA-bound catalytic intermediate in the cleavage-resealing sequence of the enzyme. Id.

New inhibitors of top 2 have been identified after they were noted for their antitumor properties. Some, such as amonafide, genistein and the terpenoides, act in the manner of the above-mentioned drugs, by trapping cleavable complexes. Antitumor compounds like merbarone and fostriecin, by contrast, inhibit top 2 activity without stabilizing cleavable complexes.

While attempting to elucidate mechanistic issues in this field, including the nature of binding site(s) for top 2 inhibitors in the ternary complex, Macdonald (1991) formulated a composite model by superimposing structural subunits of top 2 inhibitors from the five classes of compounds mentioned previously, namely, epipodophyllotoxins, anthracyclines, acridines, anthracenediones and ellipticines. The composite, three-domain pharmacophore encompassed, inter alia, a family of hybrid structures which incorporated, respectively, substructural elements from each class of top 2 inhibitors. The "unified pharmacophore" model was not refined sufficiently, however, to allow for a priori predictions of any certainty regarding the activity, if any, of actual molecules deemed within the ambit of the composite.

SUMMARY OF THE INVENTION

It is an object of the present invention, therefore, to provide top 2 inhibitors which display properties that not only distinguish them from known inhibitor compounds but also recommend them for therapeutic uses in anticancer and antiviral contexts.

In accomplishing this object and others there has been provided, in accordance with one aspect of the present invention, compounds that inhibit topoisomerase II catalytic activity and that are represented by the following formulae (A)–(D):

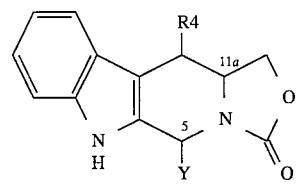
(A)

wherein
(i) Y represents the formula

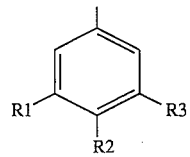

R1 and R3 are the same or different and denote, respectively, hydrogen or methoxy, and
R2 denotes hydroxyl; and
(ii) R4 denotes hydrogen, hydroxyl, alkyl ether or hydroxyalkyl ether;
In a preferred embodiment, R1 and R3 both denote methoxy and R4 denotes hydrogen;

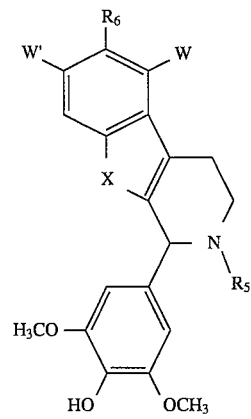
(B)

wherein
(i) X denotes NH, S or O;
(ii) R5 denotes COOCH₃, COCH₃, COCH₂OH;
(ii) R₆ denotes F, Cl, Br, CN, OH, H or NH₂; and
(iv) W and W' are the same or different and denote, respectively, H or F;

(C)

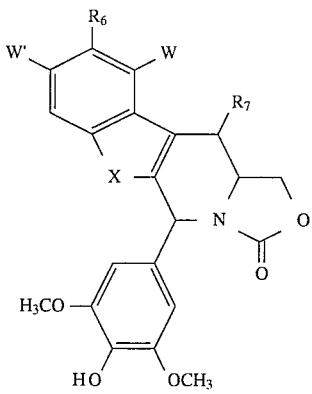

wherein
(i) X is the same as above;
(ii) W and W' are the same as above;
(iii) $R_6$ is the same as above; and
(iv) $R_7$ denotes H, OH, the formula

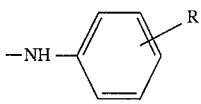

wherein

R denotes H, OH F, Br, Cl, $NO_2$, $NH_2$, CN, $OCH_3$, or $CO_2CH_2CH_3$;

the formula $$-T-(CH_2)_n Z$$

wherein

T denotes NH or O;

Z denotes $NH_2$, OH, $N(CH_3)_2$, or $N(CH_2:CH_2:Cl)_2$;

n is 2, 3 or 4; and $R_7$ may be derivatized with a 4,6 o-protected sugar;

(D)

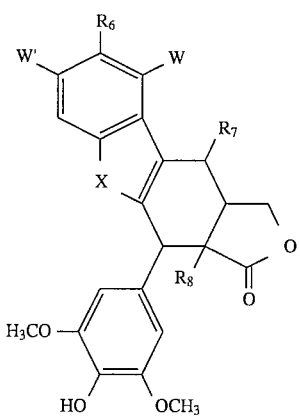

wherein
(i) X is the same as above;
(ii) W and W' are the same as above;
(ii) $R_6$ is the same as above;
(iv) $R_7$ is the same as above; and
(v) $R_8$ denotes H or OH.

The term "4,6 o-protected sugar" includes etoposide analogs such as o-glucosyl sugars protected with a conventional protecting group such as a methy acetal or a thiophene acetal group.

It has surprisingly been found that compounds of formula (C), when $R_6$ is H, $R_7$ is

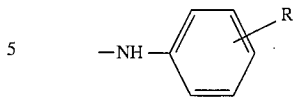

and R is F, have increased topoisomerase II catalytic activity when compared to compounds of formula (A). The activity is increased by a factor of at least 5, and preferably by at least 10, when compared to compounds of formula (A). Those skilled in the art readily recognize that the dosage amount required for compounds having such an increase in activity are respectively decreased to maintain the same or a similar effect.

In accordance with another aspect of the present invention, a pharmaceutical composition is provided that comprises a tumor-affecting amount of a compound represented by formula (A), (B), (C) or (D), and a physiologically compatible carrier for that compound. In one preferred embodiment, the pharmaceutical composition is an injectable or infusible preparation.

In accordance with yet another aspect of the present invention, a method is provided for treating cancer in a mammal, which method comprises the step of bringing a pharmaceutical composition as described above into contact with cancerous tissue in a mammal suffering from a tumor, such that neoplastic development in the cancerous tissue is retarded or arrested. Thus, preferred modes of administration in the context of such a method are those that maximize contact between cancerous tissues and the active agent of the pharmaceutical composition.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

A new class of top 2 poisons has been discovered which, despite certain structural similarities to demethylepipodophyllotoxins and other known top 2 inhibitors, are distinguishable in terms of DNA cleavage pattern and structure-activity relationships which could not have been predicted from any structural superimposition of known anthracycline, acridine, epipodophyllotoxin and anthracenedione structures. Archetypical of the new class of inhibitors is the compound azatoxin and derivatives thereof, 5R,11aS-3-one-1H,6H,-5,4,11,11a-tetrahydro-5-(3,5-dimethoxy-4-hydroxyphenyl) -oxazolo[3',4':1,6]pyrido[3,4,-b]indole, which is represented by formula (A) above when R1 and R3 are methoxy, R2 is hydroxyl and R4 is hydrogen.

Compared to other top 2 inhibitors, azatoxin induces the largest number of top 2 cleavage sites both in SV40 and c-myc DNA, and is very active in inducing protein-linked DNA breaks in cells. Accordingly, azatoxin and other pharmacophores of the present invention should be useful as reagents in the context of mapping top 2 sites in chromatin.

Figure 1B:
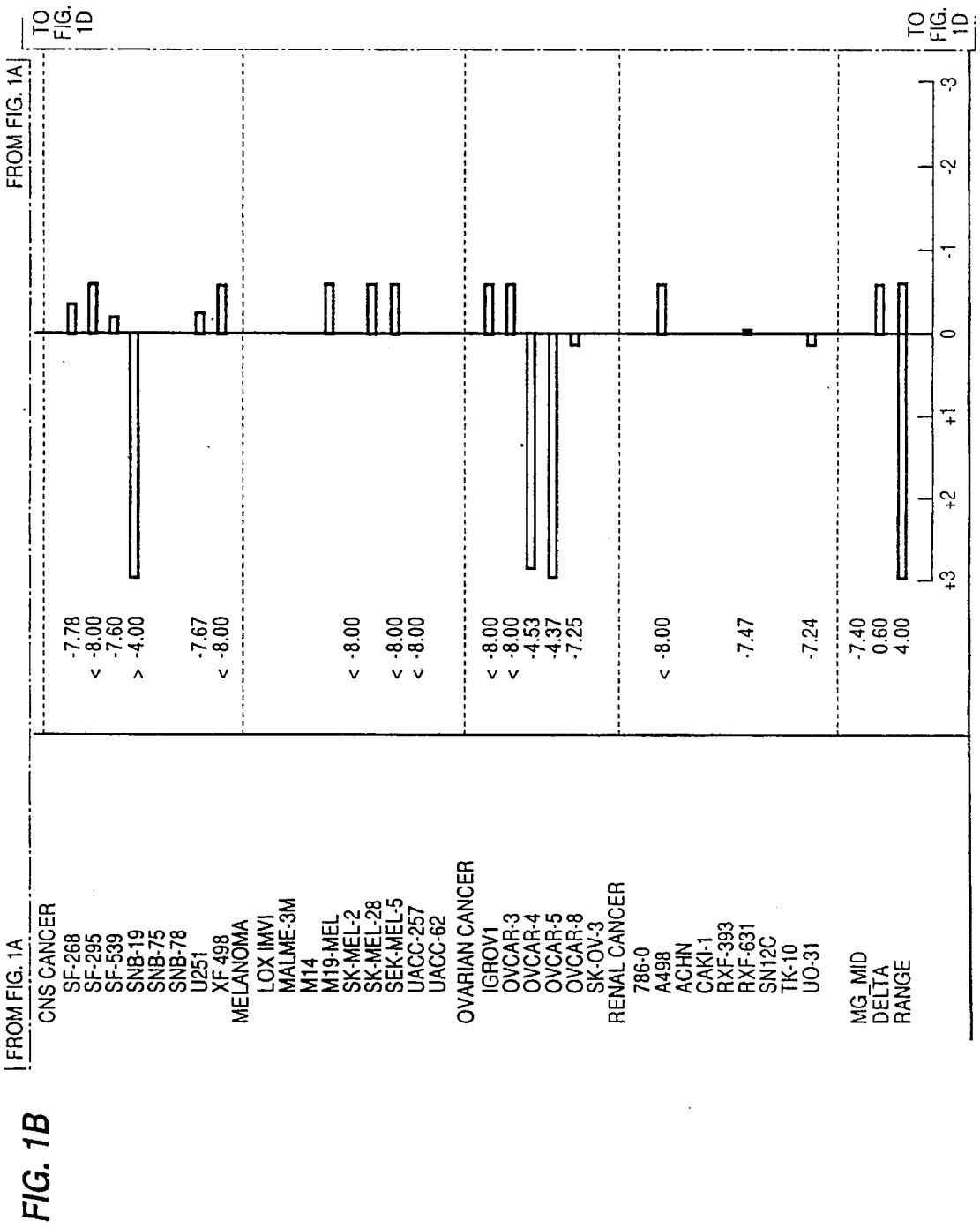
FIG. 1 is a graphical representation of results generated by testing the inhibitory activity of an illustrative compound within the present invention against panel of tumor cell lines which is a standard of the National Cancer Institute Developmental Therapeutics Program [GI50: "50% growth inhibition"; TGI: "tumor growth inhibition"; LC50: "50% lethal concentration"].
Figure 1C:
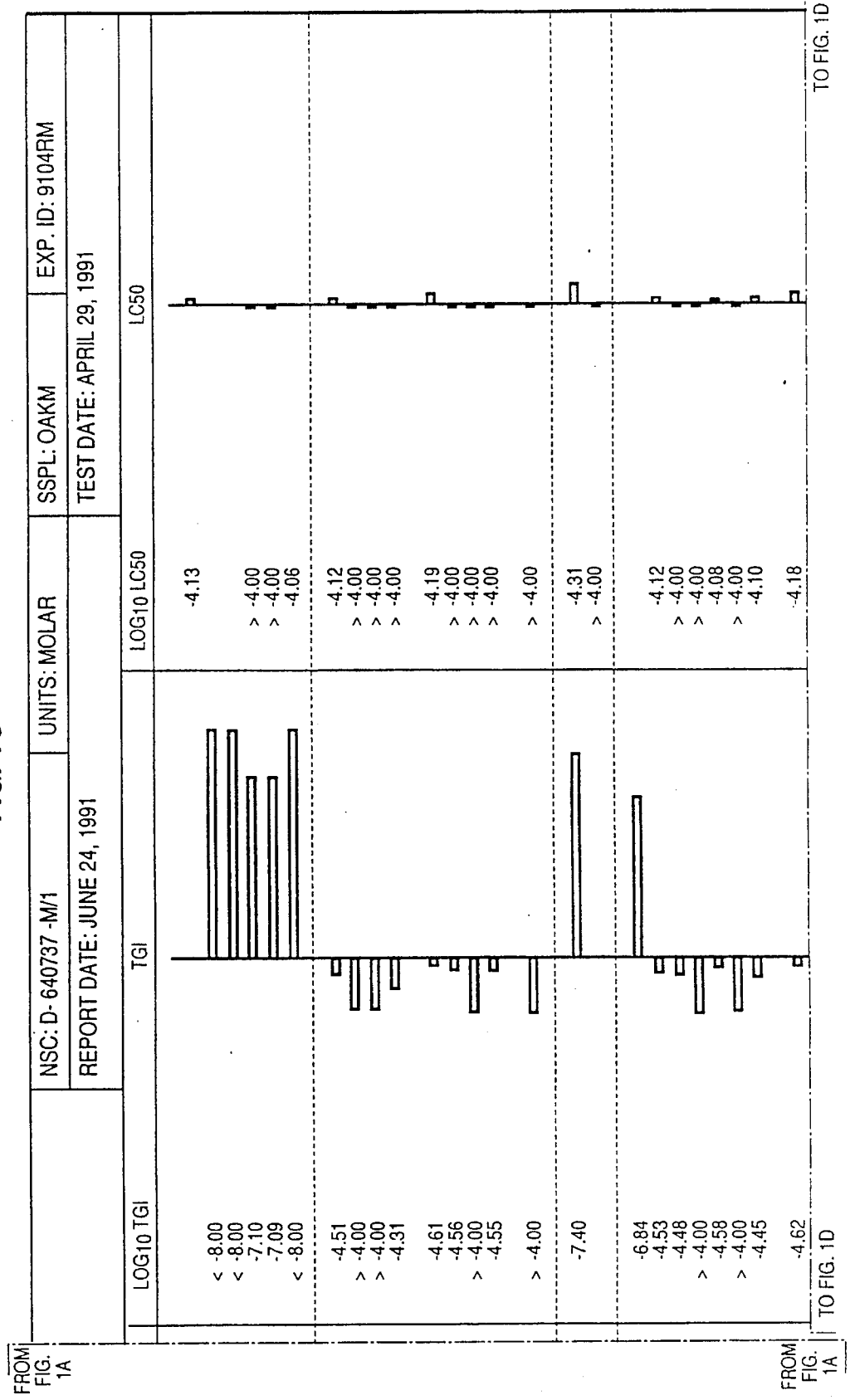
Figure 2:
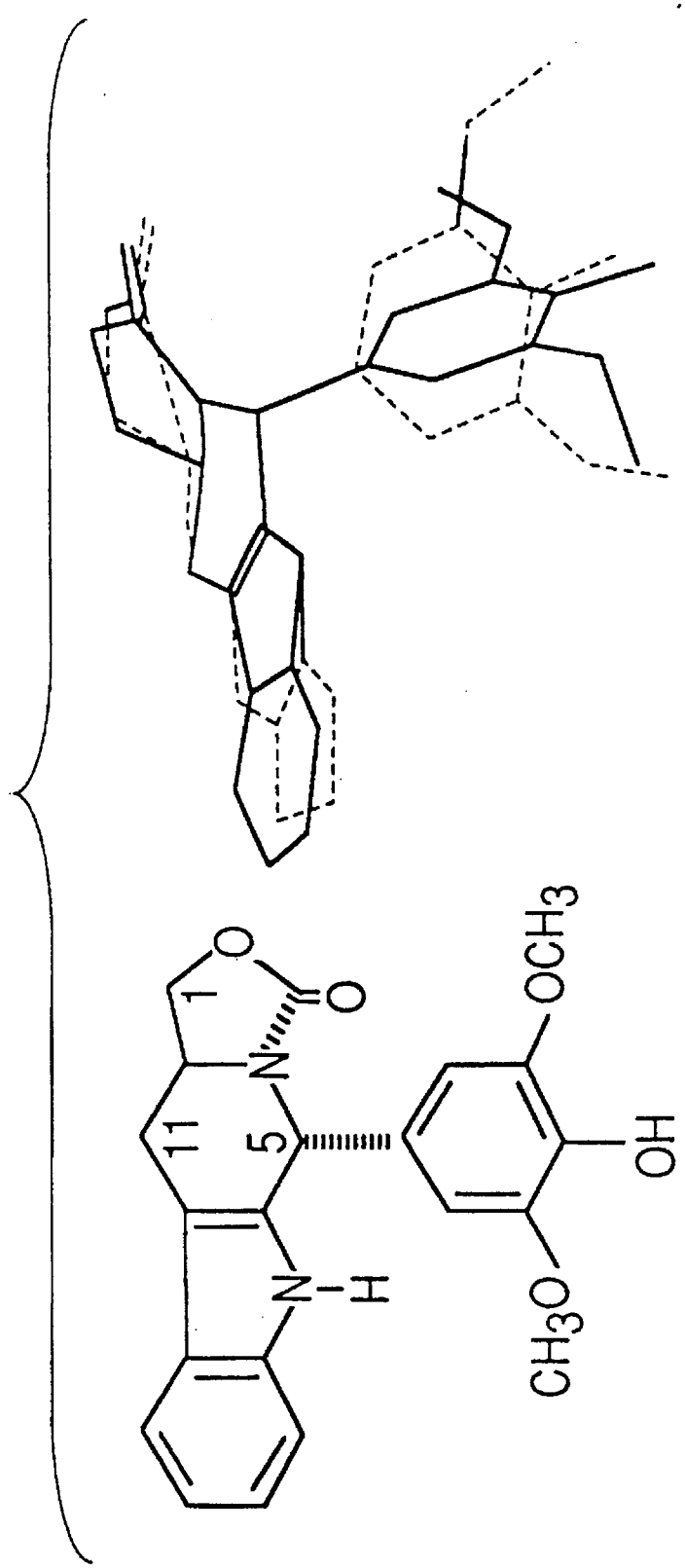
FIG. 2 depicts, at left, the structural formula of a preferred compound of the present invention (azatoxin) and, at right, a stereochemical superimposition of the top 2 poison demethyldesoxy-podophyllotoxin (DMDP; dashed lines) and azatoxin (solid lines).

Azatoxin also displays a pattern of differential growth inhibition against human tumor cell lines which is indicative of an antitumor drug action reminiscent of that of top 2 poisons like the nonintercalative epipodophyllotoxins, VP-16 (etoposide) and VM-26 (teniposide). See Yang et al., *Cancer Res.* 45:5872–76 (1985), and Liu (1989), supra, at 361–63. More specifically, azatoxin evidenced significant inhibitory activity when screened against a panel of sixty human tumor cells lines representing leukemia and melanoma, as well as cancers of the lung, colon, kidney, ovary and central nervous system. Pursuant to the convention of Paull et al., *J. Nat'l Cancer Inst.* 81:1088–92 (1989), the contents of which are hereby incorporated by reference, FIG. 1 depicts these results, in terms of parameters conventional to cancer research, by graphs which are centered at the arithmetic mean of the logarithm of each parameter. See also Monks et al., *J. Nat'l Cancer Inst.* 83: 757–66 (1991), and Boyd, *Principles & Practice of Oncology* 3:1–12 (1989).

Since a right-extending bar in such a "means graph" indicates a sensitivity by the cell line to the test substance, FIG. 1 evidences the cytotoxicity of aratoxin to cells associated with disseminated cancers (leukemias) as well as several consolidated cancers (non-small cell lung and colon). It also has been discovered, using a conventional in vitro tubulin polymerization assay, that azatoxin is a potent tubulin inhibitor in the manner of several compounds, such as vincristine, vinblastine and taxol, that are very active in cancer chemotherapy. Thus, azatoxin effectively prevents tubulin polymerization in vitro at concentrations in the range of 1 to 10 µM.

Compounds of the present invention can be synthesized via a modified Pictet-Spengler reaction. More specifically, the inventive compounds are obtained by reacting a corresponding pendent-group dimethylacetal with a precursor carbamate in the presence of a catalytic amount of para-toluenesulfonic acid.

Because the azatoxin skeleton is synthetically accessible, a large number of derivatives are readily prepared and screened for top 2 inhibitory activity in accordance with the present invention. Such screening can be effected by means of an in vitro assay which employs purified top 2 and $^{32}$P-end-labelled DNA. In such an assay, top 2 inhibition by a test substance results in DNA fragmentation which can be detected by agarose gel electrophoresis, as described by Fesen and Pommier, *J. Biol. Chem.* 19:11354–59 (1989); by the filter-binding assay described by Pommier et al., *Biochem.* 24:6410–16 (1985); or by the sodium dodecylsulfate precipitation assay employed by Nelson et al., *Proc. Nat'l Acad. Sci. USA* 81: 1361–65 (1984).

Although a myriad of azatoxin derivatives may be synthesized, the structure-activity relationships illuminated in this description indicate that those derivatives falling within the present invention will conform to certain guidelines of molecular design. Thus, with reference to formula (A) and FIG. 1, there should be a conservation of the relative spatial orientation between the polycyclic ring system and the pendant ring (Y) in azatoxin. The R/S stereochemistry of the polycyclic ring system also should be carried over from azatoxin. Methoxy groups at the 3' and 5' positions (R1 and R3, respectively) enhance top 2 inhibition, while a 4' hydroxyl group (R2) is essential for inhibitory activity. In contrast to R2, greater flexibility is realized at the 11R position (R4), where substitutions of the preferred hydrogen can be a hydroxyl group, an alkyl ether group or a hydroxyalkyl ether group such as ethoxyethyl and hydroxypropyl.

The present invention also contemplates the use of compounds according to formulae (A), (B), (C) and (D) in a pharmaceutical composition which further comprises a physiological compatible carrier for the compound. The phrase "physiological compatible carrier" here denotes a solid, liquid or gaseous material that can be used as a vehicle for administering a formula (A), (B), (C), or (D) compound as a medicament because the material is inert or otherwise medically acceptable, as well as compatible with the active agent, in a particular context of administration. In addition to a suitable excipient, a physiologically compatible carrier can contain conventional additives such as diluents, adjuvants, antioxidants and other preservatives, solubilizing agents, and the like.

The preferred routes for administering a pharmaceutical composition of the present invention are those that maximize introduction of the active agent into the immediate region of the tumor under treatment. It is advantageous, therefore, that the pharmaceutical composition should be an injectable or infusible preparation, the formulation of which would typically require initial solubilization in a nonaqueous solvent, such as dimethyl sulfoxide (DMSO), that is employed in the field to accommodate hydrophobic anticancer agents. Similarly, intraarterial administration is preferred for therapy when the tumor is supplied by a known artery, while intrathecal administration can be used for tumors located in the brain.

Intradermal and intracavitary administration is feasible with tumors that are restricted to areas close to a particular skin region and particular portion of the body cavity, respectively. By the same token, an active agent of the present invention can be administered via application to a mucosal lining (sublingually, for example), when the tumor is accessible through the lining, or via inhalation or insufflation with a gaseous carrier, when the tumor is accessible to the respiratory tract. It is possible, furthermore, to administer an active agent of the present invention in a topical preparation applied to a superficial tumor or, more generally, to a lesion associated with a viral infection against which compounds of the present invention prove effective.

Alternatively, an inventive pharmaceutical preparation can be in a form suitable for oral administration (cachet, tablet, hard- and soft-gelatin capsule, etc.). This route takes advantage of the targeting afforded by the particular sensitivity of proliferating, neoplastic cells to the cytoxic effects of the inventive compounds.

A pharmaceutical composition of the present invention also can take the form of a solid dosage preparation (implant) for introduction surgically into the tumor or its immediate vicinity. A so-called "implantation tablet" would be made up primarily of the active substance and, hence, could be absorbed completely. On the other hand, an implant featuring a non-absorbable skeleton (plastic matrix) or coating would effect controlled release of the inventive compounds upon implantation and then would be removed from the tissues after ceasing to exert an antitumor influence.

A pharmaceutical composition within the present invention preferably contains an inventive compound in an amount that itself is tumor-inhibiting or, in the context an infusion regimen, that permits accumulation in the tumor of a cytotoxic level of the active agent. Since an inventive compound typically inhibits both topoisomerase II activity and tubulin polymerization, it is possible to realize a therapeutic spectrum combining aspects both of a top 2 poison like doxorubicin and a tubulin inhibitor like vincristine. See GOODMAN AND GILLMAN'S THE PHARMACOLOGICAL BASIS OF THERAPEUTICS (7th ed. 1985), at pages 1279–85, the contents of which are hereby incorporated by reference. Symptoms of clinical toxicity associated with these two types of anticancer agents also may be observed and, if so, will require remedial countermeasures which are conventional to the field of cancer therapy.

From these considerations it will be apparent that the optimum dosage of the inventive compound will vary with the particular case. The relevant pharmacokinetics can be determined routinely in the clinical context, which may be therapeutic or prophylactic. "Therapeutic treatment" in this context means treatment intended to kill a maximum number of neoplastic cells, while a "prophylactic treatment" is one aimed at retarding or preventing re-establishment of a proliferating neoplastic population and, hence, a relapse in the disease, once remission has been achieved. It is anticipated that a typical dosage regimen will be similar to that of etoposide (VP-16), i.e., on the order of 100 mg/m$^2$ per day.

Without further elaboration, it is believed that those skilled in the art, informed by the preceding description, can utilize the present invention fully. Accordingly, the following examples are presented for purposes of illustration only. The materials and methods employed in the examples are described below:

Chemicals, and enzymes: Azatoxin and its derivatives, as well as the demethyldesoxypodophyllotoxin (DMDP) and demethylepipodophyllotoxin (DMEP), were synthesized by conventional methods. The compounds m-AMSA and mitoxantrone were obtained from the Drug Synthesis and Chemistry Branch, National Cancer Institute, Bethesda, Md. The compounds VP-16 and VM-26 were obtained from Bristol-Myers Company (Wallingford, Conn.). Drug stock solutions were made in dimethylsulfoxide at 10 mM. Further dilutions were made in distilled water. Various other reagents, including simian virus 40 (SV40) and c-myc human DNA inserts in plasmid pBR322, restriction endonucleases, DNA topoisomerase I, T4 polynucleotide kinase, calf intestine phosphatase, agarose and polyacrylamide/bis, were purchased from Bethesda Research Laboratories (Gaithersburg, Md.), from the American Type Culture Collection (Rockville, Md.) or from New England Biolabs (Beverly, Mass.). [Gamma-$^{32}$P]ATP was purchased from New England Nuclear Research Products (Boston, Mass.).

DNA topoisomerase II was purified from mouse leukemia L1210 cell nuclei as described, for example, by Pommier et al. (1985), supra, and was stored at −70° C. in 40% (v/v) glycerol, 0.35 M NaCl, 5 mM MgCl$_2$, 1 mM KH$_2$PO$_4$, 0.2 mM dithiothreitol and 0.1 mM phenylmethanesulfonyl fluoride (pH 6.4). The purified enzyme yielded a single 170 kDa band after silver staining of SDS-polyacrylamide gels, in accordance with the description of Pommier et al., *Cancer Res.* 46: 3075–81 (1986).

Preparation of end-labeled DNA fragments: DNA fragments were 5' end-labeled as described, for example, by Fesen and Pommier (1989), supra. Briefly, native DNA was first linearized with a restriction enzyme, then the 5'-DNA first linearized with a restriction enzyme, then the 5'-DNA termini were dephosphorylated with calf alkaline phosphatase and labeled with [gamma-$^{32}$P]ATP using T4 polynucleotide kinase. For double-strand breaks assays using HL-60 nuclear extract, SV40 DNA was digested with BclI endonuclease and labeled at both DNA termini. For sequencing experiments, SV40 and c-myc DNAs were first 5'-end labeled at the XhoII and XbaI restriction sites, respectively. Then, in order to generate uniquely 5'-end-labeled fragments, labeled DNA was subjected to a second enzyme digestion, PflMI for SV40, and EcoRI plus HindIII for c-myc DNA. The resulting DNA fragments were separated by agarose gel electrophoresis and isolated by electroelution. Purification by phenol-chloroform extraction and ethanol precipitation were included between each step and at the end of the labeling procedures, pursuant to Pommier et al., *J. Molec. Biol.* 222: 909–24 (1991).

Topoisomerase II-induced DNA cleavage reactions: DNA fragments were equilibrated with or without drug in 10 mM Tris-HCl, pH 7.5, 50 mM KCl, 5 mM MgCl$_2$ 0.1 mM EDTA, 1 mM ATP and 15 µg/ml bovine serum albumin for 5 minutes before addition of purified topoisomerase II (40 to 70 ng) or HL-60 nuclear extract in 20 µl final reaction volume. Reactions were stopped by adding sodium dodecyl sulfate (SDS) to a final concentration of 1% and proteinase K to 400 µg/ml, followed by incubation for 1 hour at 40° C.

For agarose gel analysis, 3 µl (10×) loading buffer (0.3% bromophenol blue, 16% Ficoll, 10 mM Na$_2$HPO$_4$) was added to each sample which was then heated at 65° C. for 1–2 minutes before loading into an agarose gel made in (1×) TBE (89 mM Tris, 89 mM boric acid, 2 mM EDTA, pH8), in accordance with Fesen & Pommier (1989), supra. Agarose gel electrophoresis was conducted overnight at 2 V/cm. The quantification of drug-induced DNA double-strand breaks in the presence of HL-60 nuclear extract was effected as described in the next paragraph.

Radioactive gels were counted in betascope 603 blot analyzer. For each lane radioactivity then was measured in the DNA cleavage products (C) (size between 600–5243 bp), and in the total DNA present in the lane with a size superior to 600 bp (T). Drug-induced cleavage was expressed as:

$$\text{Percent DNA cleaved} = 100 \times \frac{C/T - C_\circ/T_\circ}{1 - C_\circ/T_\circ}$$

where $C_\circ$ and $T_\circ$ are the counts for cleaved and total DNA, respectively, in presence of nuclear extract without drug.

For DNA sequence analysis, samples were precipitated with ethanol and resuspended in 2.5 µl loading buffer (80% formamide, 10 mM NaOH, 1 mM EDTA, 0.1% xylene cyanol and 0.1% bromophenol blue). Samples were heated to 90° C. and immediately loaded into DNA sequencing gels (6% polyacrylamide; 19:1, acrylamide:bis) containing 7M urea in (1×) TBE buffer. Electrophoresis was at 2500 V (60 W) for 4 hours. Gels were dried on 3M paper sheets and autoradiographed with Kodak XAR-2 film. See Pommier et al. (1991), supra.

EXAMPLE 1

SYNTHESIS OF AZATOXIN AND OTHER COMPOUNDS

1H NMR spectra were taken on a General Electric QE300 Spectrometer at 300 MHz. Mass spectra were recorded on a Finnegan MAT4615 GC/MS/DS instrument using chemical or electron impact ionization techniques. Elemental analyses were determined by Atlantic Microlab Inc. (Norcross, Ga.). Melting points were determined on a Thomas-Hoover UNI-MELT apparatus and are uncorrected.

Thin-layer chromatography was performed using E. Merck glass plates pre-coated with silica gel 60 F-254 and visualized with a phosphomolybdic acid/ethanol solution. Woelm silica 32–63 was employed for column chromatography which was carried out using a modified short/flash column technique.

Tetrahydrofuran was distilled from sodium benzophenone immediately prior to use. Dichloromethane was distilled from $CaH_2$ immediately before use. All chemicals were purchased from Aldrich Chemical Company except for D and L-tryptophan methyl ester-HCl, which was purchased from Sigma Chemical Company.

All reactions were carried under an argon atmosphere.
4S-(1H Indol-3-ylmethyl)-2-oxazolidone (Compound 1A):

Sodium (1.56 g, 68.1 mmol) was dissolved in absolute ethanol (150 ml) and 1-trptophanol (12.94 g, 68.02 mmol) in ethanol (100 ml) and diethyl carbonate (8.83 g, 74.8 mmol) were added. The solution was heated at reflux for 5 hours and was concentrated after cooling. Saturated $NH_3Cl$ (100 ml) and $CH_2Cl_2$ (200 ml) were added, and after mixing well the layers were separated. The organic layer was washed with $CH_2Cl_2$ (2×100 ml) and the organic fractions were combined, dried over $Na_2SO_4$, and concentrated. Recrystallization from $MeOH/H_2O$ yielded 11.66 g (79%) of a white solid: mp $155_0$C; $_1$NMR ($CDCL_3$) 8.17(sb, 1H) 7.57(d, J=7.94 Hz, 1H), 7.40(d, J=8.06 Hz, 1H), 7.19(m, 2H), 7.08(d, J=2.2 Hz, 1H), 5.22(sb, 1H), 4.50 (m, 1H), 4.21 (m, 2H), 3.04 (m, 2H). $[g]^{24}{}_D$+8.4 (c 9.4, MeOH). Anal. ($C_{12}H_{12}N_2O_2$) C, H, N.
4R- (1H- Indol-3-ylmethyl)-2-oxazolidone:

This compound was prepared in a manner analogous to the preparation of Compound 1a. $[a]^{24}{}_D$–8.3 (c 1.25, MeOH), Anal. ($C_{12}H_{12}N_2O_2$) C, H, N.
General Method for the Preparation of Dimethyl Acetals To a solution of the aromatic aldehydes (1 g) in trimethyl orthoformate (7 ml) a catalytic amount of p-TSOH (40 mg) was added and the reaction was followed to completion by TLC. The solvent was removed under reduced pressure and the remaining oil was dissolved in $CHCl_2$ and filtered through a plug of silica. The solvent was again removed under reduced pressure and the remaining oil was stored in a desiccator until use.
Preparation of 5,11a-trans-aza toxins:

Method A

To a solution of Compound 1a (2 mmol) and the corresponding aldehyde (2 mmol) in a $CH_2Cl_2/MeOH$ (9:1) solution (6 ml) was added concentrated $H_2SO_4$(4 mmol). The reaction was followed to completion by TLC (20% acetone in $CHCL_3$). The solution was added to sat $NaHCO_3$, the layers were separated, and the aqueous layer was washed with $CH_2Cl_2$ (3×). The combined organic fractions were dried over $Na_2SO_4$, filtered and concentrated. The product was purified by flash chromatography (acetone-$CH_2Cl_2$).

Method B

To a solution of the corresponding dimethyl acetal (2.2 mmol) and Compound 1a (2 mol) in $CHCl_3$ (8 ml), p-toluenesulfonic acid (.0.2 mmol) was added. The reaction was followed to completion by TLC. If the reaction proceeded too slowly the reaction was heated at reflux.

Saturated $NaHCO_3$ was added. The layers were separated, and the aqueous layer was washed with $CH_2Cl_2$ (2×20 ML). The organic layers were combined, dried over $Na_2SO_4$, filtered and concentrated. The product was purified by flash chromatography (acetone-$CH_2Cl_2$).

Method C

To a solution of the corresponding dimethyl acetal (3 mmol) and Compound 1a (2 mmol) in anhydrous THF (8 ml), anhydrous TFA (10 mmol) was added and the solution was heated at reflux. The reaction was followed to completion by TLC. After cooling, the solution was added to saturated $NaHCO_3$, the layers were separated, and the aqueous layer was washed with $CH_2Cl_2$(3×20 ml). The combined organic fractions were dried over $Na_2SO_4$, filtered and concentrated. The product was purified by flash chromatography (acetone-$CH_2Cl_2$).

5R, 11aS-3-One-5,4,11,11a-tetrahydro-5-(3,5-dimethoxy-4-hydroxyphenyl) -1H, 6H-oxazolo[3', 4': 1,6]pyrido[3,4-b]indole (Compound 1)

This compound was prepared as described in method C. Purification by flash chromatography (12% acetone in $CHCl_3$, $R_f$=0.28) produced a white solid in 91% yield: mp (decomposed slowly around 175° C.); $_1$NMR ($CD_3CN$) 7.94(sb, 1H), 7.51(d, J-7.91 Hz, 1H), 7.30(d, J=7.57 Hz, 1H), 7.09(m, 2H), 6.59(s, 2H), 6.27(s, 1H), 5.88(d, J=1.7 Hz, 1H), 4.54(dd app t, J=8.3 Hz, 1H), 4.33(m, 1H), 4.21(dd, J=8.5 Hz, 4.7 Hz, 1H), 3.75(s, 6H), 3.16, (dd, J=15 Hz, 4.6 Hz, 1H), 2.76(ddd, J=15 Hz, 10.38 Hz, 1.73 Hz, J=1.73 Hz, 1H) $[\alpha]^{22}{}_D$=-139. 6 Anal ($C_{21}$, $H_{20}$, $N_2$, $O_5$) C, H, N.

5S, 11aR-3-One-5,4,11, 11a-tetrahydro-5-(3,5-dimethoxy-4-hydroxyphenyl) -1H, 6H-oxazolo[3,4,: 1,6]pyrido[3,4-b]indole This compound was prepared in a manner analogous to the preparation of Compound 1. $[\alpha]^{22}{}_D$+139.4. Anal. ($C_{21}$, $H_{20}$, $N_2$, $O_5$) O, H, N.

5R, 11aS-3-One-5,4,11,11a-tetrahydro-5-(3-methoxy-4-hydroxyphenyl)-1H, 6H-oxazolo[3', 4': 1.6]pyrido[3,4-b]indole (Compound 2)

This compound was prepared as described in method A. Purification by flash chromatography (15% acetone in $CHCl_3$, $R_f$=0.30) gave a white solid in 40% yield: $^1$NMR ($CD_3CN$) 8.94(s, 1H), 7.51 (d, J=7.59 Hz, 1H), 7.29(d, J=7.95 Hz, 1H), 7.09(m, 2H), 6.91(d, J=1.7 Hz, 1H,), 6.79(d, J=8.08 Hz, 1H), 6.74(dd, J=8.08 Hz, 1.7 Hz 1H), 6.55 (sb, 1H), 5.90(d, J=1.5 Hz, 1H), 4.52(dd app t, J=7.94 Hz, 1H), 5.27(m. 1H), 4.20(dd, J=8.21 Hz, 4.83 Hz, 1H), 3.78 (s, 3H), 3.16 (dd, J=14.93 Hz, 8.48 Hz, 1H), 3.77(ddd, J=14.91 Hz, 10.07 Hz, 1.59 Hz, 1H). Anal. ($C_{20}H_{18}N_2O_4$) C, H, N.

5R, 11aS-3-one-5,4,11,11a-tetrahydro-5-(4-hydroxyphenyl)-1H, 6H-oxazolo[3',4':1,6]pyrido[3,4-b]indole (Compound 3)

This compound was prepared as described in method C. Purification by flash chromatography (20% acetone in $CHCl_3$, $R_f$=0.28) followed by recrystallization from $CH_3CN$ gave a white solid in 89% yield: $_1$NMR ($d_6$-DMSO) 9.47(s, 1H), 7.43 (d, J=7.56 Hz, 1H), 7.24(d, J=7.91 Hz, 1H), 6.99(m, 4H), 6.70 (d, J=8.6 Hz, 2H), 5.81(s, 1H), 4.49(dd app t, J=8.03 Hz, 1H), 4.14(m, 2H), 3.10(dd, J=12.14 Hz, 4.69 Hz, 1H), 2.68 (dd, J=14.3 Hz, 10.6 Hz, 1H). Anal. ($C_{19}$,$H_{16}$, $N_2$, $O_3$/$CH_3CN$) C, H, N.

5R,11aS-3-one-5,4,11,11a,tetrahydro-5-(3,4,5-trimethoxyphenyl)-1H, 6H-oxazolo[3',4':1,6]pyrido[3,4-b]indole (Compound 4)

This compound was prepared as described in method C. Purification by flash chromatography (7% acetone in $CHCl_3$, $R_f$=0.30) yielded a white solid in 91% yield: mp 203° C., $^1$NMR ($CD_3CN$) 8.95(s, 1H), 7.51(d, J=7.64 Hz, 1H), 7.31(d, J=7.93 Hz, 1H), 7.09(m, 2H), 6.61(s, 2H), 5.89(s, 1H), 4.57(dd app t, J=8.24 Hz, 1H), 4.35(m, 1H), 4.23(dd, J=8.42 Hz, 4.68 Hz, 1H), 3.74(s, 6H), 3.70(s, 3H), 3.17(dd, J=15.02 Hz, 4.48 Hz, 1H), 2.77(dd, J=14.85 Hz, 10.41 Hz, 1H).

Methyl-3-(1-benzenesulfonyl-indol-2-yl)-2-amino-propanoate (Compound 8a)

This compound was prepared, according to the method of Schollkopf et al., *Angew, Chem. Int. Ed. Engl.* 18:863 (1979), using (1-benzenesulfonyl)-2-chloromethyl-indole (Compound X) and 2,5-diethoxy-3,6-tetrahydropyrazine (Compound Y) as starting materials. 'H NMR (CDCl$_3$) 8,19(d,1H), 7,79(d, 2H), 7,55–7,18(m, 6H), 6.51(s,1H), 4,19(q, 2H), 4,00(dd, 1H), 3.55(dd, 1H), 1.18(t, 3H).

3-(1-benzenesulfonyl-indol-2-yl)-2-aminopropanol (Compound 8b)

To a well-stirred solution of 0.44 g (4.1 eq.) NaBH$_4$ in 20 mL 75% ethanol, 0.85 g (8a) in 10 mL 75% ethanol was added and the solution heated at reflux 15 hours. TLC showed no starting material. The solution was allowed to cool and then it was diluted with 20 mL water and the ethanol was removed by rotary evaporation. The residue was extracted with ethyl acetate (4×20 mL), dried over sodium sulfate, and concentrated to yield 0.56 g (56%) of Compound 8b as a clear oil which was used without further purification. 'H NMR (CDCl$_3$) 8.18(d, 1H), 7.71(d, 2H), 7.60-7.19(m, 6H), 6.50(s, 1H), 3.70(m, 1H), 3.50(dd, 1H), 3.45(dd, 1H), 3.25(dd, 1H), 2.90(dd, 1H).

1H-Indol-2-ylmethyl-2-oxazolidone (Compound 8c)

To a solution of 0.07 g (1.5 eq) Na dissolved in 5 mL absolute ethanol, 0.67 g of Compound 8b in 10 mL absolute ethanol and 0.36 g (1.5 eq) diethyl carbonate were added and the solution was heated at reflux overnight (16 hours). TLC showed a higher R$_f$ spot(80:20) ethyl acetate: hexane, R$_f$=0.35). After cooling the ethanol was evaporated by rotary evaporation and the residue was diluted with 15 mL saturated ammonium chloride and extracted with CH$_2$C$_2$ (3×20 mL). Purification by flash chromatography using an 80:20 ethyl acetate: hexane mixture as eluent yielded 0.22 g (71%) of Compound 8c as a tan solid. 'H NMR(CDCl$_3$) 8.85 (s, 1H), 7.55(d, 1H), 7.30(d, 1H), 7.15(m, 2H), 6.45(s, 1H), 6.20(g, 1H), 4.30(m, 1H), 4.00(m, 2H), 2.82(d, 2H).

5,11a-trans-3-one-5,4,11, 11a-tetrahydro-5-(3,5-dimethoxy-4-hydroxyphenyl-1H, 10H-oxazolo[3',4':1,6]pyrido[4,3-b]indole (Compound 8)

To a solution of 0.7 g (1.5 eq) syringealdehyde dimethyl acetal and a few grains p-TSOH in 2 mL CH$_2$Cl$_2$ was added 0.04 g of Compound 8c. The solution was stirred for 2 hours. TLC showed no starting material. The solution was concentrated and purified by flash chromatography using a 15% acetone in chloroform solution as eluent to yield 0.05 g(69%) of Compound 8 as a beige solid. 'H NMR(CDCN) 9.28(bs, 1H), 7.40(d, 1H), 7.15(t, 1H), 7.00(d, 1H), 6.92(t, 1H), 6.58(s, 2H), 6.22(bs, 1H), 5.98(s, 1H), 4.47(t, 1H), 4.31(m, 1H), 4.16(q, 1h), 3.69(s, 6H), 3.11(dd, 1H), 2.91(ddd, 1H).

Racemic methyl-3-(acenapth-1-yl)-2-aminopropanoate (Compound 7a)

This compound was synthesized according to the method of Schollkopf et al., *Liebigs Ann. Chem.* 1987: 393–97, using acenapthylene-1-carboxaldehyde (Compound Z) and 2,5-diethoxy-3,6-tetrahydropyrazine (Compound Y) as starting materials. The final product was synthesized in an identical manner as described for Compound 8. Due to the substitution in the 4-position, however, the intermediates existed as an inseparable mixture of diastereomers and 'H NMR analysis proved impossible, except for identification of important groups.

5,11a-trans-3-one-5, 4, 11, 11a-tetrahydro-5-(3,5-dimethoxy-4-hydroxyphenyl)-1H, 10H-oxazol [3', 4':1,6]pyrido[1, 2-b]acenapthylene (Compound 7)

0.01 mL BP$_3$OEt$_2$ was added to a solution of 0.03 g of Compound 7d and 0.01 mL triethyl silane in 1 mL CH$_2$Cl$_2$ at −78° C. The solution was warmed slowly to room temperature over a period of 2 hours. TLC showed no starting material. 5 mL H$_2$O was added, the layers were separated, and the aqueous layers were extracted with 2×5 mL portions of CH$_2$C$_2$, dried and concentrated. The residue was purified by flash chromatography using a 15% acetone in chloroform solution as eluent to yield 19.4 mg (70%) of Compound 7. 'H NMR (CDCl$_3$) 7.81 (d, 1H), 7.71(d, 1H), 7.65–7.51(m, 2H), 7.38(t, 1H"), 7.11(d, 1H), 6.72(s, 2H), 6.14(d, 1H), 5.52(s, 1H), 4.58(t, 1H), 4.25(m, 2H), 3.77(s, 6H), 3.24(dd, 1H), 2.90(ddd, 1H).

1R,3R-1-(3-5-dimethoxy-4-hydroxyphenyl)-3-methoxycarbonyl-1,2,3,4-tetrahydro-β-carboline(Compound 9A)

To a solution of 1-tryptophan methyl ester hydrochloride (9.52 g, 37.4 mmol) in CHCl$_3$(150 ml) was added 14% ammonium hydroxide (30 ml). The biphasic mixture was allowed to stir for 1 hour. The layers were separated and the aqueous layer was extracted with CHCl$_3$ (2×100 ml). The organic layers were combined, dried over Na$_2$SO$_4$, and concentrated to yield a yellow oil. The oil was dissolved in benzene (200 ml). Syringaldehyde (6.81g, 37.4 mmol) and Na$_2$SO$_4$(10 g) were added, and the solution was allowed to stir for 60 hours. A white precipitate formed. The mixture was again concentrated, and anhydrous CH$_2$Cl$_2$ (150 ml) and anhydrous TFA (5.76 ml, 74.8 mmol) were added at 0° C. The solution was allowed to stir at 0° C for 12 hours. The mixture was again concentrated, and the remaining solid was added to a biphasic mixture of saturated NaHCO$_3$ and ether. The mixture was allowed to stir for 1.5 hours and the white solid that formed was collected in a sintered glass funnel. The solid was washed with water, dried in a vacuum oven, and recrystallized from CH$_3$CN/water to produce 13.34 g (93%) of a white solid: Anal. (C$_{21}$, H$_{22}$, N$_2$, O$_3$) C, H, N.

1S, 3S-1-(3,5-dimethoxy-4-hydroxyphenyl)-3-methoxycarbonyl-1,2,3,4-tetrahydro-β-carboline This compound was prepared in a manner analogous to the preparation of Compound 9A. Anal. (C$_{21}$, H$_{22}$, N$_2$, O$_5$) C, H, N.

1R, 3R-1-(3,5-dimethoxy-4-hydroxyphenyl)-3-hydroxymethyl-1,2,3,4-tetrahydro-β-carboline (Compound 9B)

To a solution of Compound 9a (2.01 g, 5.31 mmol) in 1:1 dioxane/water (20 ml) NaBH$_1$(1.00 g, 26.6 mmol) was added, and the solution was allowed to stir at room temperature for 3 hours. The solvent was removed under reduced pressure and the remaining solid was redissolved. The product was precipitated by the addition of NaCl, and collected by filtration and dried in a vacuum dessicator to yield 1.43 g (76%) of a white solid which was used without further purification.

1S,3S-1-(3,5-dimethoxy-4-hydroxyphenyl)-3-hydroxymethyl-1,2,3,4-tetrahydro-β-carboline This compound was prepared and analyzed in a manner analogous to the preparation of Compound 9B.

5R,11aR-3-One-5,4,11,11a-tetrahydro-5-(3,5-dimethoxy-4-hydroxyphenyl)-1H, 6H-oxazolo[3'4':1,6']pyrido[3,4-b]indole (Compound 9)

To a suspension of the amino-alcohol (1.31 g 3.70 mmol) in THF (10 ml), carbonyl diimidazole (1.79 g, 11.1 mmol) was added and the suspension was allowed to stir for 5 hours. The suspension was concentrated and 10% NaOH was added. After stirring for an additional 3 hours, the solution was Carefully acidified to pH 6 by the addition of concentrated HCl and the resulting mixture was extracted with EtOAc (3×50 ml), dried over Na$_2$SO$_4$ and concentrated. $^1$NMR (CDCl$_3$) 7.58(s, 1H), 7.51(d, J=8.37 Hz, 1H), 7.19(m, 3H), 6.57(s, 2H), 5.52(s, 1H), 5.24 (s, 1H), 4.63 (t, J=6.65, Hz, 1H), 4.22(m, 2H), 3.83(s, OH), 3.22(m, 1H), 2.92(ddd, J=16.4 Hz, J=10.1 Hz, J=1.8 Hz, 1H). Anal ($C_{21}$, $H_{20}$, $N_2$, $O_5$) C, H, N.

5S, 11aS-3-One-5,4,11,11a-tetrahydro-5-(3,5-dimethoxy-4-hydroxyphenyl)-1H, GH-oxazolo[3'4':1,6]pyrido[3,4-b]indole (Compound 10)

This compound was prepared in a manner analogous to the preparation of Compound 9. Anal. ($C_{21}$, $H_{20}$, $N_2$, $O_5$) C, H, N.

5R,11R,11aS-3-One-11-methoxy-5,4,11,11a-tetrahydro-5-(3,5-dimethoxy-4-hydroxyphenyl)-1H, 6H-oxazolo [3'4':1,6]pyrido[3,4-b]indole (Compound 1C)

To a solution of syringaldehyde dimethyl acetal (0.50 g) and catalytic p-toluenesulfonic acid in anhydrous $CH_2Cl_2$/MeOH 9:1(8 ml), Compound 1B was added at 0° C. in small portions. After stirring for 4 hours the precipitate that formed was collected by filtering the reaction mixture through a sintered glass funnel, and was dried in a vacuum desiccator to yield the pure product in 47% yield. $^1$NMR ($d_6$-DMSO) 8.42 (sb, 1H), 7.65 (d, 1H), 7.31(d, 1H), 7.06(m, 2H), 6.48(s, 2H), 5.85(s, 1H), 4.63(d, J=1.8 Hz, 1H), 4.43(m, 3H), 3.64(s, 6H), 3.28(s, 3H).

5R,11R,11aS-3-One-11-hydroxy-5,4,11,11a-tetrahydro-5-(3,5-dimethoxy-4-hydroxyphenyl)-1H, 6H-oxazolo[3'4':1,6]pyrido[3,4-b]indole (Compound 6)

To a suspension of Compound 1c (1mmol) in water (8 ml) KIOH (2mmol) was added, and the solution was brought to reflux and immediately cooled. The solution was then acidified to ph 7 with 10% HCl, and the precipitate that formed was collected by filtration in a sintered glass funnel and dried in a vacuum dessicator. 5R, 11R, 11aS-3-One-11-methoxy-5,4,11,11a-tetrahydro-5-(3,5-dimethoxy-4-hydroxyphenyl)-1H, 6H-oxazolo [3'4':1,6]pyrido[3,4-b]indole (Compound 1C)

To a solution of syringaldehyde dimethyl acetal (0.50 g) and catalytic p-toluenesulfonic acid in anhydrous $CH_2Cl_2$/MeOH 9:1(8 ml), Compound 1B was added at 0° C. in small portions. After stirring for 4 hours the precipitate that formed was collected by filtering the reaction mixture through a sintered glass funnel, and was dried in a vacuum desiccator to yield the pure product in 47% yield. $^1$NMR ($d_6$-DMSO) 8.42(sb, 1H), 7.65(d, 1H), 7.31(d, 1H), 7.06(m, 2H), 6.48(s, 2H), 5.85(s, 1H), 4.63(d, J=1.8 Hz, 1H), 4.43(m, 3H), 3.64(s, 6H), 3.28(s, 3H).

5R, 11R,11aS-3-One-11-methoxy-5,4,11,11a-tetrahydro-5-(3,5-dimethoxy-4-O-carbomethoxyphenyl)-1H, 6H-oxazolo [3',4':1,6]pyrido[3,4-b]indole (Compound 1D)

Compound 1C (1.96 g, 4.77 mmol) was suspended in 10 ml of $CH_2Cl_2$ and 6.7 ml (47.7 mmol) TEA. In the suspension, 3.69 ml (47.7 mmol) of methyl chloroformate was added dropwise at 0° C., the solution was diluted with $CH_2Cl_2$ and washed with water. The organic fraction was dried over $Na_2SO_4$, filtered and concentrated. Purification by flash chromatography eluting with 8% acetone in $CHCl_3$ yielded 2.09 g (94%) of a white solid. An analytical sample was obtained by recrystallization from ethyl acetate.

5R,11R,11aS-3-One-11-hydroxy-5,4,11, 11a-tetrahydro-5-(3,5-dimethoxy -4-O-carbomethoxyphenyl)-1H, 6H -oxazolo [3',4':1,6]pyrido[3,4-b]indole (Compound 1E)

To a solution of 1.88 g (7.00 mmol) of compound 1D in a 9:1 dioxane/water solution (30 ml), 130 mg (0.70 mmol) of paratoluenesulfonic acid (p-TSOH) was added. The solution was followed to completion by TLC and diluted with $CHCl_3$. The resulting mixture was washed with saturated $NaHCO_3$, dried over $Na_2SO_4$, filtered and concentrated. Purification by flash chromatography eluting with 20% acetone in $CHCl_3$ yielded 1.21 g (66%) of a white solid.

5R,11R,11aS-3-One-11-(4-fluoroanilino)-5,4,11,11a-tetrahydro-5-(3,5-dimethoxy-4-O-carbomethoxy)-1H, 6H-oxazolo [3',4':1,6]pyrido[3,4-b]indole (Compound 1F)

To a solution of 0.33 g (0.73 mmol) of Compound 1E in anhydrous dioxane (4 ml), 350 μl (2.5 mmol) of TEA and 160 μl (2.1 mmol) of acetyl chloride were added. After stirring for 15 minutes, the solvent and unreacted acetyl chloride were removed under reduced pressure. The reaction vessel was recharged with dioxane, (diethylene dioxide DDO), 1.4 mmol of 4-fluoro aniline and 1.4 mmol TEA. The reaction mixture then was heated at 50° C. and stirred for 6 hours. To this solution, $CHCl_3$ was added and the resulting solution was washed with water, dried over $Na_2SO_4$, and concentrated. Purification by flash chromatography eluting with 10% acetone in $CHCl_3$ yielded 62 mg (16%) of a white solid.

5R,11R,11aS-3-One-11-(4-fluoroanilino)-5,4,11,11a-tetrahydro-a5-(3,5-dimethoxy-4-hydroxyphenyl)-1H,6H-oxazolo[3',4':1,6]pyrido[3,4-b]indole (Compound 11)

To a solution of sodium methoxide (90 μmol) in 1 ml methanol, 16.5 mg (30 μmol) of Compound 1F was added and the reaction was followed to completion by TLC. Saturated $NH_4Cl$ (200 μl) was added followed by addition of $CH_2Cl_2$. The layers were separated and the organic layer was dried over $Na_2SO_4$, filtered and concentrated. Purification by flash chromatography eluting with 20% acetone in $CHCl_3$ yielded 10.8 mg (73%) of a white solid.

Representative syntheses for the aforementioned compounds are depicted below:

Compound 1A:

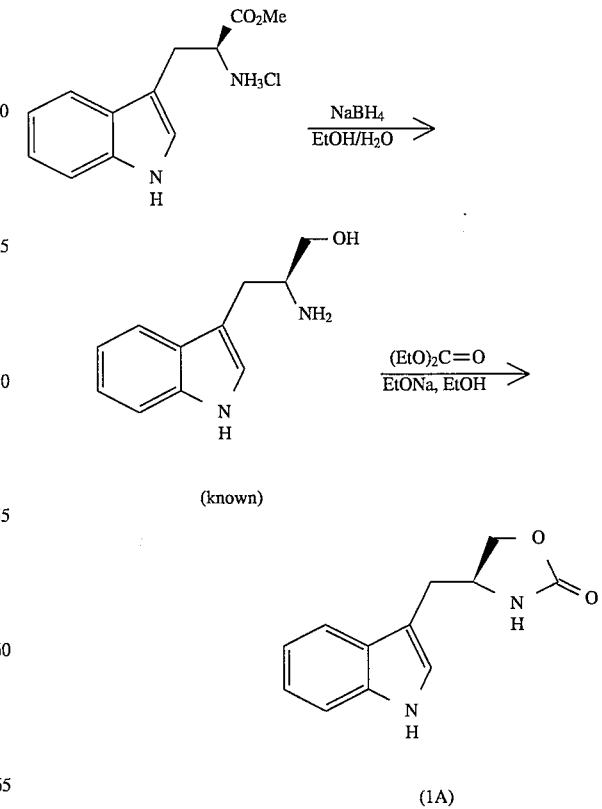

Compounds 1-5:

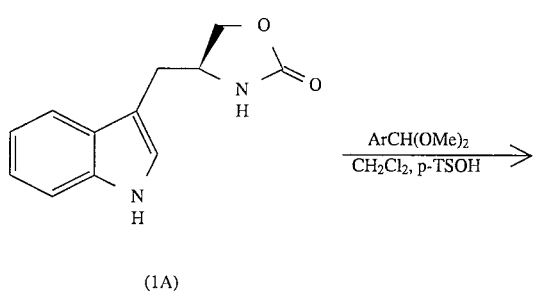

(1A)

$\xrightarrow[\text{CH}_2\text{Cl}_2,\ p\text{-TSOH}]{\text{ArCH(OMe)}_2}$

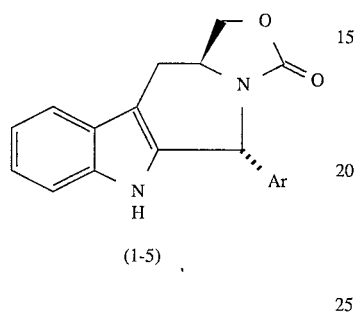

(1-5)

Wherein Ar can be Y, as defined above.

Compound 6:

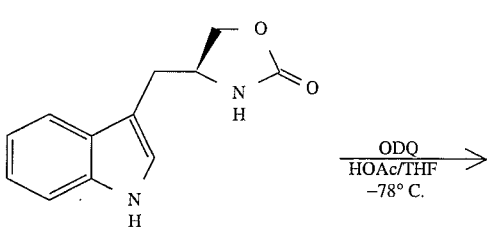

(1A)

$\xrightarrow[\substack{\text{HOAc/THF} \\ -78°\ \text{C.}}]{\text{ODQ}}$

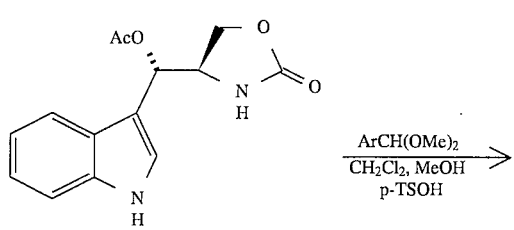

(1B)

$\xrightarrow[\substack{\text{CH}_2\text{Cl}_2,\ \text{MeOH} \\ p\text{-TSOH}}]{\text{ArCH(OMe)}_2}$

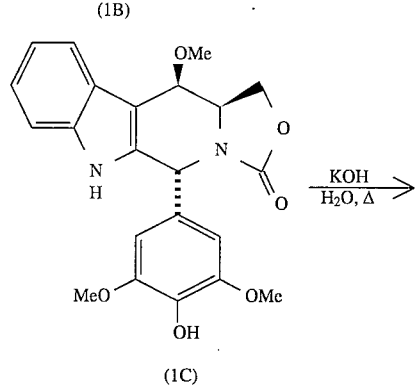

(1C)

$\xrightarrow[\text{H}_2\text{O},\ \Delta]{\text{KOH}}$

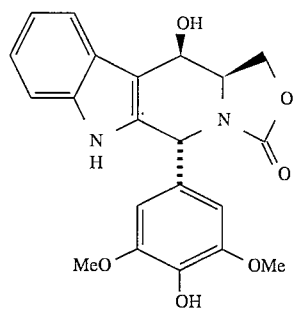

(6)

Compounds X, Y and Z have the following structures:

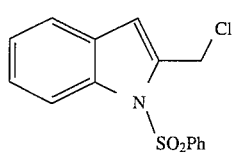 (X)

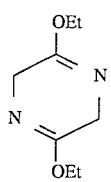 (Y)

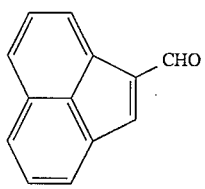 (Z)

Compound 7:

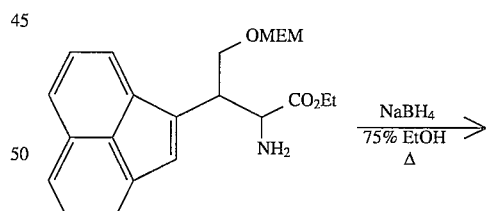

(7a)

$\xrightarrow[\substack{75\%\ \text{EtOH} \\ \Delta}]{\text{NaBH}_4}$

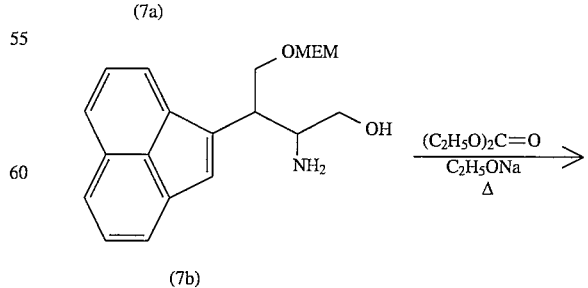

(7b)

$\xrightarrow[\substack{\text{C}_2\text{H}_5\text{ONa} \\ \Delta}]{(\text{C}_2\text{H}_5\text{O})_2\text{C}=\text{O}}$ 17
-continued
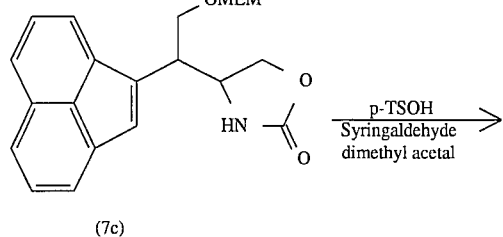
(7c)
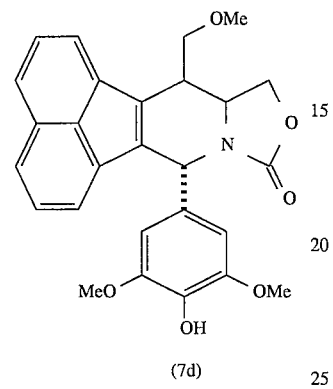
(7d)
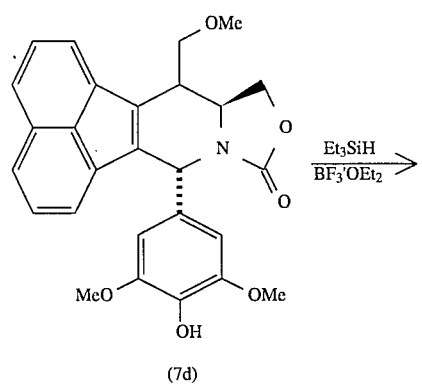
(7d)
Compound 8:
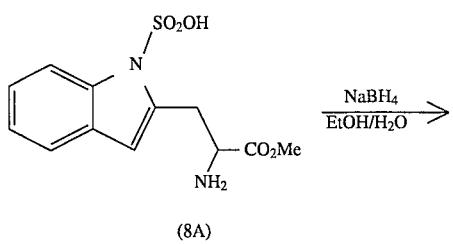
(8A)
18
-continued
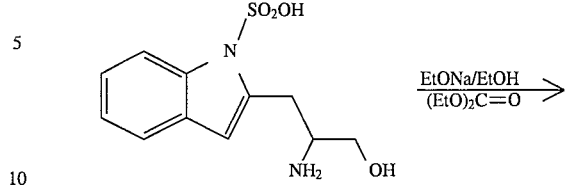
(8B)
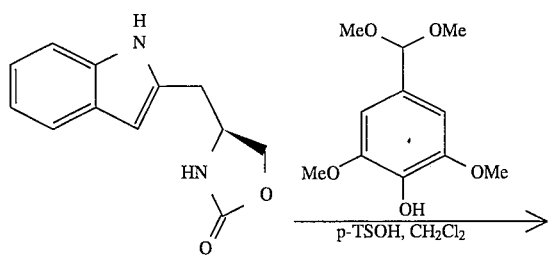
(8C)
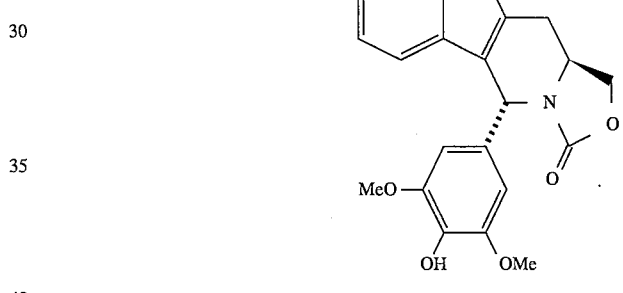
(8)
Compound 9:
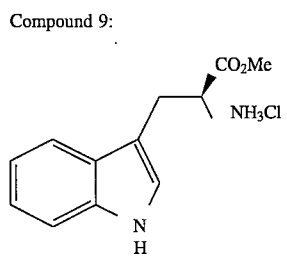
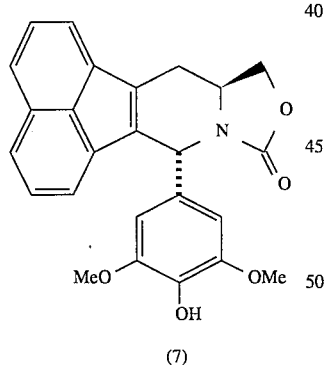
(7)
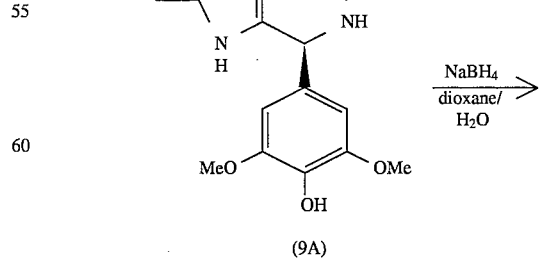
(9A)

19
-continued
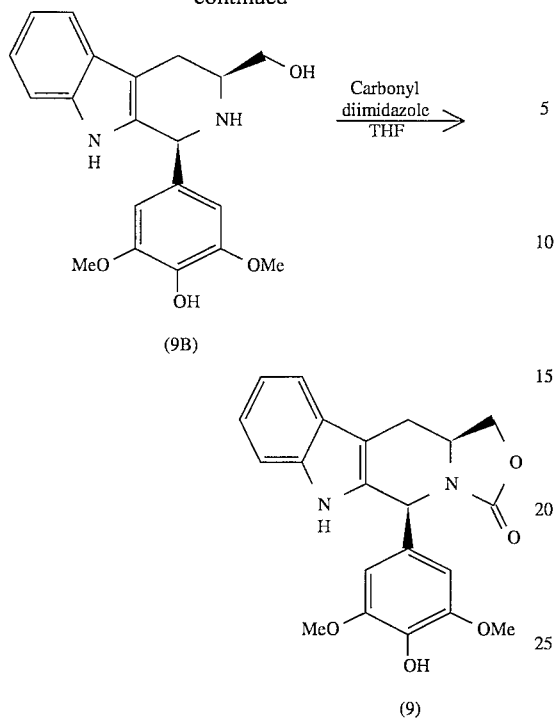
Compound 11:
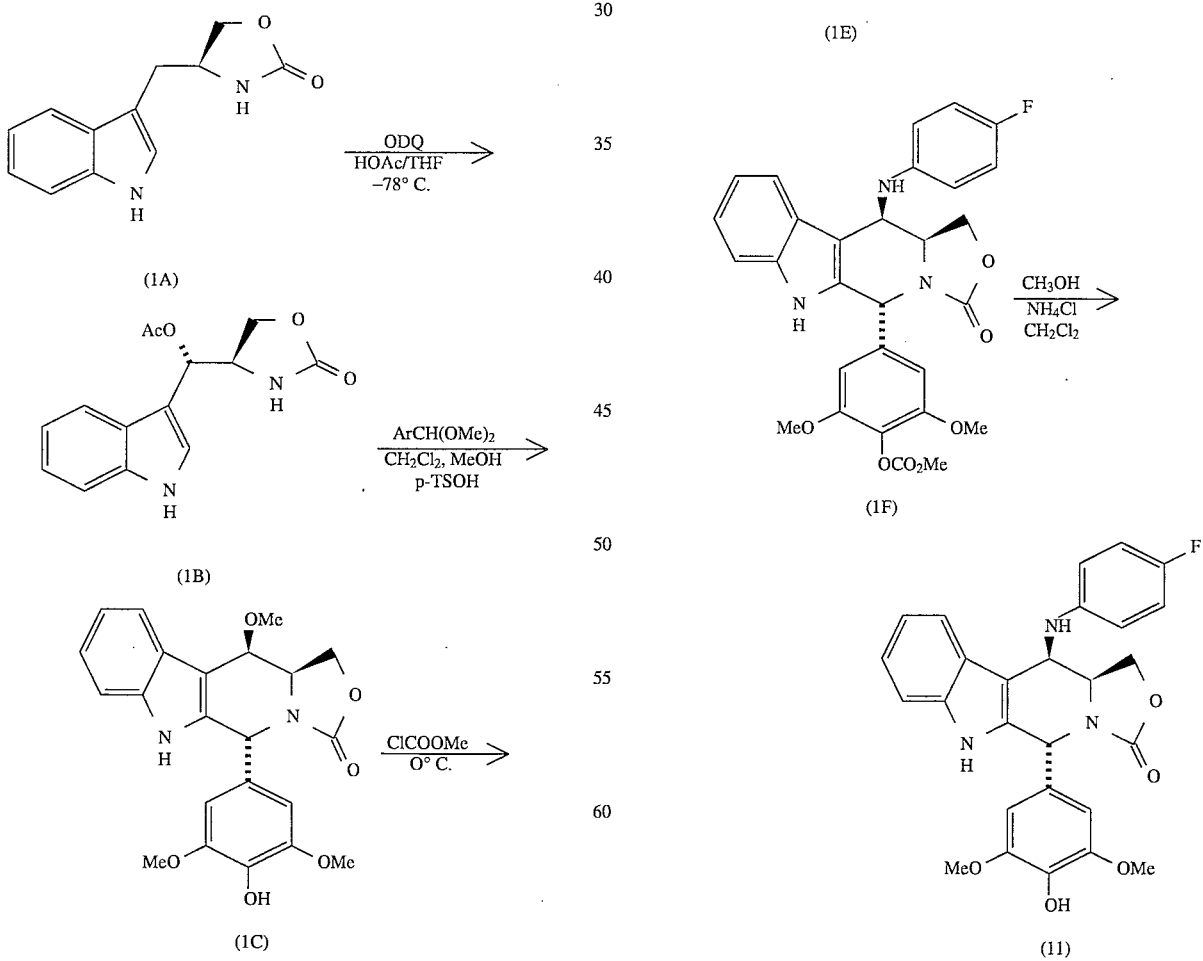
20
-continued
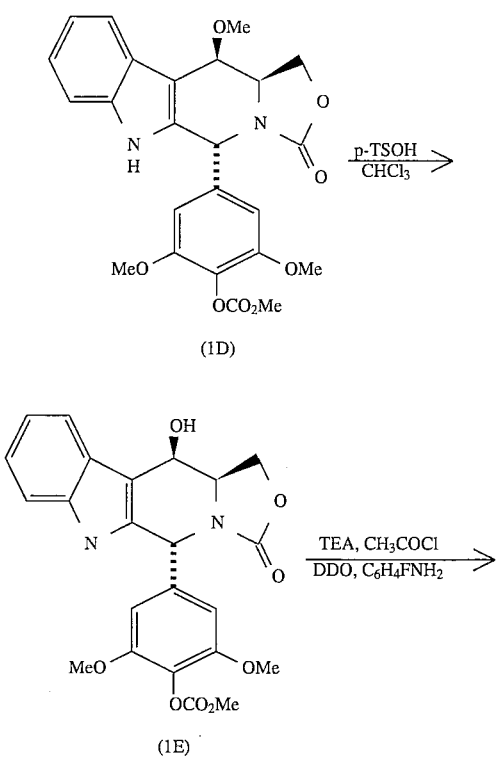

EXAMPLE 2

INDUCTION OF DNA DOUBLE-STRAND BREAKS BY AZATOXIN IN THE PRESENCE OF HL-60 NUCLEAR EXTRACT

Drug-induced DNA double-strand breaks were measured first in SV40 DNA in the presence of HL-60 nuclear extracts. SV40 DNA was chosen because it is a natural substrate of top 2 and is cleaved at many sites by other top 2 inhibitors. See, for example, Fesen & Pommier (1991), supra. The smallest azatoxin concentration that produced detectable cleavage was 5 to 10 µM. Above 10 µM, cleavage occurred at many sites and was proportional to the logarithm of azatoxin concentration. The potency of azatoxin was comparable to that of VP-16 and, as in the case of VP-16, azatoxin-induced DNA cleavage was not suppressed at high drug concentrations (up to 1 mM), consistent with azatoxin's not intercalating into DNA (see below).

EXAMPLE 3

SEQUENCING OF TOPOISOMERASE II CLEAVAGE SITES BY AZATOXIN

Induction of top 2 cleavage by azatoxin was tested directly with the use of purified murine leukemia top 2. Since the SV40 nuclear matrix-associated region has been shown to be cleaved preferentially by top 2, see Pommier et al. (1991), supra, this region was chosen for analysis. Sites of cleavage were also determined by DNA sequencing in the 5' flank of c-myc first intron. Azatoxin induced many cleavage sites both in the SV40 and the c-myc DNA fragments. In general, azatoxin induced more cleavage sites than mitoxantrone, m-AMSA, VM-26 or VP-16. Thus, azatoxin was shown to be a potent top 2 inhibitor, with a cleavage pattern differing from those induced by other top 2 inhibitors.

The cleavage pattern of azatoxin also was compared to that of epipodophyllotoxin derivatives the structures of which seem quite similar (for drug structures and abbreviations, see table below). The compound 4'-demethyl-4-desoxypodophyllotoxin (DMDP), with a structure most similar to azatoxin, induced less cleavage that azatoxin and at distinct cleavages sites. The β-4-hydroxy derivative of DMDP, 4'-demethylepipodophyllotoxin (DMEP), was at least as potent as VP-16, and its cleavage patterns, while similar to that of VP-16 with some local differences, was different from that of azatoxin.

EXAMPLE 4

EFFECTS ON TOPOISOMERASE ACTIVITY

Two different assays were conducted to illuminate the nature of azatoxin's effects vis-à-vis DNA relaxation. To study the inhibition of top 2 catalytic activity, topoisomerase reactions were performed with 0.4 µg native SV40 DNA in 30 µl reaction buffer for 30 minutes at 37° C. and stopped by adding SDS to a final concentration of 1% and proteinase K to 400 µg/ml, followed by incubation for 1 hour at 42° C., essentially as described by Fesen & Pommier (1989), supra. Agarose gel electrophoresis was performed in 1% gels made in Tris-Acetate-EDTA (TAE) buffer (40 mM Tris-Acetate, pH 7.6, 10 mM $Na_2EDTA$). Gels were run at 2 V/cm overnight, washed in water and then stained with 1 µM ethidium bromide for 45 minutes. After an additional 45 minutes destaining in 1 mM $Mg_2SO_4$, the DNA was visualized under UV light and photographed with a Polaroid type 57 film.

To assess DNA unwinding, see Pommier et al., Nucleic Acids Res. 15: 6713–31(1987), the DNA was relaxed first by treatment for 15 minutes with top 1 (20 units), after which the test agent was added. These steps were carried out at 37° C. DNA-agent-top 1 mixtures were incubated for an additional 30 minutes and then stopped as described above. Samples were then subjected to agarose gel electrophoresis as described above.

From the assay data it was determined that azatoxin inhibits top 2-mediated relaxation of native SV40 DNA. At the same time, azatoxin was observed to produce a substantial amount of linear DNA without significant increased of nicked DNA.

The DNA unwinding assay, with excess topoisomerase I and relaxed SV40 DNA, was employed to assess azatoxin intercalation in accordance with Pommier et al., Nucleic Acids Res. 15:6713–31 (1987) In fact, azatoxin did not induce detectable DNA unwinding even at drug concentrations as high as 1 mM. This was also the case for the 2 azatoxin isomers, 8 and 10, and for the demethylepipodophyllotoxins, DMDP and DMEP. Similar results were obtained with supercoiled DNA. The lack of unwinding by azatoxin strongly indicated that the drug does not intercalate into DNA.

EXAMPLE 5

EFFECTS OF AZATOXIN STRUCTURAL MODIFICATIONS ON TOPOISOMERASE II INHIBITION

Three isomers and six azatoxin derivatives, the synthesis of which is described in Example 1, were tested for drug-induced cleavage efficiency in the presence either of HL-60 extract or of purified top 2. The compounds and test results are set out in the table below.

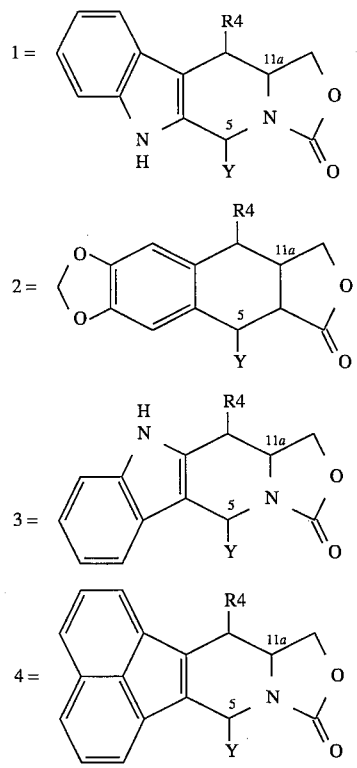

-continued

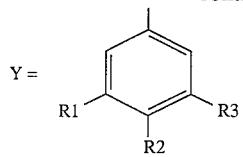

| COMPOUND | STRUCTURE | Y | | | | Stereochemistry | | Topoisomerase II |
|---|---|---|---|---|---|---|---|---|
| | | R1 | R2 | R3 | R4 | 5 | 11a | inhibition |
| AZATOXINS | | | | | | | | |
| Azatoxin | 1 | OCH3 | OH | OCH3 | H | R | S | +++ |
| 2 | 1 | H | OH | OCH3 | H | R | S | o |
| 3 | 1 | H | OH | H | H | R | S | O |
| 4 | 1 | OCH3 | OCH3 | OCH3 | H | R | S | O |
| 5 | 1 | H | NHSO2CH2 | H | H | R | S | O |
| 6 | 1 | OCH3 | OH | OCH3 | OH | R | S | + |
| 7 | 4 | OCH3 | OH | OCH3 | H | R | S | O |
| 8 | 3 | OCH3 | OH | OCH3 | H | R | S | O |
| 9 | 1 | OCH3 | OH | OCH3 | H | R | R | O |
| 10 | 1 | OCH3 | OH | OCH3 | H | S | S | O |
| EPIPODOPHYLLOTOXINS | | | | | | | | |
| DMDP | 2 | OCH3 | OH | OCH3 | H | R | S | + |
| DMEP | 2 | OCH3 | OH | OCH3 | OH | R | S | +++ |
| VP-16 | 2 | OCH3 | OH | OCH3 | a | R | S | +++ |
| VM-26 | 2 | OCH3 | OH | OCH3 | b | R | S | ++++ |

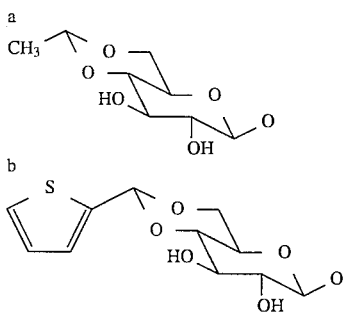

Azatoxin Isomers

The three azatoxin isomers (compounds 8–10 in the table) were found not to be active as top 2 inhibitors in DNA cleavage assays. The finding that the two diastereoisomers (9 and 10) were inactive demonstrated that a strict stereochemical relationship between the polycyclic ring system and the pendant aromatic ring must exist for activity. The inactivity of isoazatoxin (8) was surprising and indicated the great sensitivity of the binding site for these agents to minor structural modification. Thus, azatoxin and isoazatoxin (8) differ only in the orientation of the tetrahydrooxazolopyrido ring fusion into the indole ring; this change in orientation imparts (1) only a subtle differential "curve" to the tetracyclic nucleus of the molecule, without altering the spatial relationship between the indole and phenyl ring systems, and (2) a change in orientation of the nitrogen indole.

Azatoxin Derivatives

The results from testing the six azatoxin derivatives for top 2 inhibition also are set out in table. Two of derivatives were modified on the polycyclic ring system and the others were modified on the pendant ring.

Hydroxylation at position 11 (R4) of the azatoxin polycyclic ring system yielded a compound (6) that was structurally similar to DMEP and that displayed measurable but not strong top 2 activity. This 4-hydroxy substitution differentiates azatoxin from the 4'-demethylpodophyllotoxin framework, since hydroxyl substitution at this site significantly decreases top 2 activity of azatoxin (1 versus 6) and increases activity of the podophyllotoxins (DMDP, DMEP). Differing from azatoxin by its polycyclic ring system, Compound 7 is inactive, again indicating that the structure of the polycyclic ring system is critical for azatoxin activity.

Modification to the pendant (Y) ring gave the following results. Monodemethoxylation (2) reduced top 2 activity by a factor 10, while didemethoxylation (3) abolished the top 2 activity. Position 4' (R2) was also crucial as methylation of the hydroxyl residue abolished top 2 inhibition. These results are not inconsistent with those obtained for demethylepipodophyllotoxins. See, for example, Sinha et al., *Eur. J. Cancer* 26: 590–93 (1990). Notably, compound in which the azatoxin pendant ring had been placed by that of AMSA was inactive. These results differentiate the azatoxin family of top 2 inhibitors from the m-AMSA family of inhibitors.

What is claimed is:

1. A compound that inhibits topoisomerase II catalytic activity and that is represented by the following formula (C):

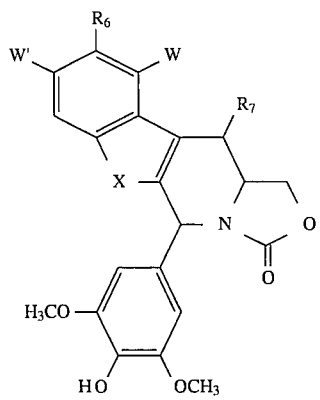

wherein
(i) X denotes NH;
(ii) $R_6$ denotes F, Cl, Br, CN, OH, $NH_2$ or H;
(iii) $R_7$ denotes H, OH, the formula

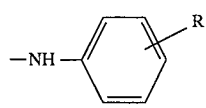

wherein
R denotes H, OH, F, Br, Cl, $NO_2$, $NH_2$, CN, $OCH_3$, or $CO_2CH_2CH_3$;
$R_7$ also denotes the formula

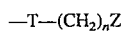

wherein
T denotes NH or O; Z denotes $NH_2$, OH, $N(CH_3)_2$, or $N(CH_2CH_2Cl)_2$; n is 2,3 or 4; and
$R_7$ may be derivatized with a 4,6 o-protected sugar; and
(iv) W and W' are the same or different and denote, respectively, H or F, provided that if $R_6$ is H, then $R_7$ denotes the formula (C)

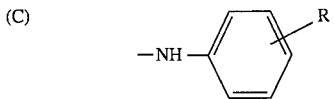

wherein
R denotes H, OH, F, Br, Cl, $NO_2$, $NH_2$, CN, $OCH_3$, or $CO_2CH_2CH_3$; or —T—$(CH_2)_n$Z wherein
T denotes NH or O; Z denotes $NH_2$, OH, $N(CH_3)_2$, or $N(CH_2CH_2Cl)_2$; n is 2, 3 or 4.

2. A compound according to claim 1, wherein $R_6$ denotes F.

3. A compound according to claim 1, wherein $R_6$ denotes Br.

4. A compound according to claim 1, wherein $R_6$ is H.

5. A compound according to claim 1, wherein $R_7$ is

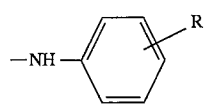

wherein R denotes F.

6. A compound according to claim 1, wherein $R_6$ is H, and $R_7$ is $NH(CH_2)_2N(CH_3)_2$.

7. A pharmaceutical composition comprising a tumor-affecting amount of a compound according to claim 1 and a physiologically compatible carrier therefor.

8. A pharmaceutical composition according to claim 7, wherein said composition is an injectable or infusible preparation.

9. A method of treating cancer in a mammal, comprising the step of bringing a pharmaceutical composition according to claim 7 into contact with cancerous tissue in a mammal that is suffering from a tumor, such that neoplastic development in said cancerous tissue is retarded or arrested.

* * * * *